United States Patent [19]
Rudslahti et al.

[11] Patent Number: 4,879,237
[45] Date of Patent: Nov. 7, 1989

[54] USE OF PEPTIDES IN CONTROL OF CELL ATTACHMENT AND DETACHMENT

[75] Inventors: Eric I. Ruoslahti, Rancho Santa Fe; Edward G. Hayman, Oceanside; Michael D. Pierschbacher, San Diego, all of Calif.

[73] Assignee: La Jolla Cancer Research Foundation, La Jolla, Calif.

[21] Appl. No.: 738,078

[22] Filed: May 24, 1985

[51] Int. Cl.[4] ............................................. C12N 5/00
[52] U.S. Cl. .......................... 435/240.2; 435/240.21; 530/331
[58] Field of Search ................. 435/68, 240.2, 240.25, 435/240.21; 530/329, 330, 331

[56] References Cited

U.S. PATENT DOCUMENTS 4,578,079  3/1986  Rouslahti et al. .................. 530/330

OTHER PUBLICATIONS

Pierschbacher, M. D. et al., "Variants of the Cell Recognition Site of Fibronectin that Retain Attachment--Promoting Activity", *P.N.A.S.*, vol. 81, (Oct. 1984), pp. 5985-5988.

Pierschbacher, M. D. et al., "Cell Attachment Activity of Fibronectin Can Be Duplicated by Small Synthetic Fragments of the Molecule", *Nature*, vol. 309, (May 3, 1984), pp. 30-33.

Effects of Fibronectin-Related Peptides on Cell Spreading Silnutzer, I. E. and Barnes, D. W., 1985, In Vitro, 21:73-78.

Isolation and Biological Characterization of Active Fragments of the Adhesive Glycoprotein Fibronectin, Hahn, L-H. E. and Yamada, K. M., (1979), Cell 18:1043-1051.

Substrate Adhesion of Rat Hepatocytes: on the Mechanism of Attachment to Fibronectin, Johansson et al., 1984, Cell Bilo., 98:810-817.

*Primary Examiner*—Elizabeth C. Weimar
*Attorney, Agent, or Firm*—Pretty, Schroeder, Brueggemann & Clark

[57] ABSTRACT

A method of using synthetic cell attachment-promoting peptides from fibronectin to detach cultured cells from the substratum is described.

9 Claims, 8 Drawing Sheets

USE OF PEPTIDES IN CONTROL OF CELL ATTACHMENT AND DETACHMENT

FIELD OF THE INVENTION

This invention related generally to the field of biochemistry and more particularly to a method for the detachment of cell lines from their substratum.

BACKGROUND OF THE INVENTION

Fibronectin is a well characterized, extracellular, structural glycoprotein which interacts with other extracellular matrix molecules and promotes cell attachment and spreading (Ruoslahti, et al., 1981; Hynes and Yamada, 1982; Furcht, 1983). The ability of cells to bind to fibronectin can now be accounted for by the tripeptide L-arginyl-glycyl-L-aspartic acid (Arg-Gly-Asp), a sequence which is found in the cell attachment domain of fibronectin (Pierschbacher, et al., 1983; Pierschbacher and Ruoslahti, 1984a; 1984b). Small synthetic peptides containing this sequence promote cell attachment when used to coat a surface and inhibit the attachment of cells to fibronectin-coated substrata when presented in a soluble form (Pierschbacher and Ruoslahti, 1984a; 1984b).

Fibronectin is not the only adhesion-promoting molecule in the immediate environs of cells (Kleinman, et (Terranova, et al., 1980; Carlsson, et al., 1981), vitronectin (Hayman, et al., 1983; Barnes and Silnutzer, 1983), and molecules such as those identified by polyclonal (Damsky, et al., 1983 and monoclonal (Oesch and Birchmeier, 1982) antibodies may also contribute to adhesion.

References

The content of the following references is incorporated into the foregoing specification as fully as though set forth therein as background for those skilled in the art.

Aggeler, J., Frisch, S. M. and Werb, Z. (1984) Changes in cell shape correlate with collagenase gene expression in rabbit synovial fibroblasts. J. Cell Biol. 98, 1662-1671.

2. Barnes, D. and Sato, G. (1980) Serum-free cell culture: a unifying approach. Cell 22, 649-655.

3. Barnes, D. W. and Silnutzer, J. (1980) Isolation of human serum spreading factor. J. Biol. Chem. 258, 12548-12552.

4. Boucaut, J. C., Darribere, T., Poole, T. J., Aoyama, H., Yamada, K. M. and Thiery, J. P. (1984) Biologically active synthetic peptides as probes of embryonic development: a complete peptide inhibitor of fibronectin function inhibits gastrulation in amphibian embryos and neural crest cell migration in avian embryos. J. Cell Biol. 99, 1822-1830.

5. Carlsson, R. N. K., Engvall, E., Freeman, A., and Ruoslahti, E. (1981) Laminin and fibronectin in cell adhesion: Enhanced adhesion of cells from regenerating liver to laminin. Proc. Natl. Acad. Sci. U.S.A. 78, 240-2406.

6. Damsky, C. H., Richa, J., Solter, D., Knudsen, K. and Buck, C. A. (1983) Identification and purification of a cell surface glycoprotein mediating intercellular adhesion in embryonic and adult tissue. Cell 4, 455-466.

7. Edelman, G. M. (1984) Cell adhesion and morphogenesis: The Regulator Hypothesis. Proc. Natl. Acad. Sci. U.S.A. 81, 1460-464.

8. Furcht, L. (1983) Structure and function of the adhesive glycoprotein fibronectin. Mod Cell Biol. 1, 53-117.

9. Furthmayr, H. (1981). Immunochemistry of the extracellular matrix. pp. 143-178, CRC Press, Inc., Boca Raton, Fla.

10. Gimbrone, M. A., Cotran, R. S. and Folkman, J. (1974) Human vascular endothelial cells in culture. Growth and DNA synthesis. J. Cell Biol. 60, 67-684.

11. Gospodarowicz, D., Delgado, D. and Vlodavsky, I. (1980) Permissive effect of the extracellular matrix on cell proliferation in vitro. Proc. Natl. Acad. Sci. U.S.A. 77, 4094-4098.

12. Hayman, E. G., Engvall, E. and Ruoslahti, E. (1981) Concomitant loss of cell surface fibronectin and laminin. J. Cell Biol. 88, 352-357.

13. Hayman, E. G., Pierschbacher, M. D., Ongren, Y. and Ruoslahti, E. (1983) Serum spreading factor (vitronectin) is present at the cell surface and in tissues. Proc. Natl. Acad. Sci. U.S.A. 80, 400-4007.

14. Hessle, H. and Engvall, E. (1984) Type VI collagen. Studies on its localization, structure, and biosynthetic form with monoclonal antibodies. J. Biol. Chem. 259, 3955-3961.

15. Hynes, R.0. (1981) relationships between fibronectin and the cytoskeleton. In: CYTOSKELETAL ELEMENTS AND PLASMA MEMBRANE ORGANIZATION. (Poste, G., and Nicolson, G. L., eds.), Elsevier/North-Holland, pp. 1OO-137.

16. Hynes, R. O. and Yamada, K. M. (1982) Fibronectins: multifunctional modular glycoproteins. J. Cell Biol. 95, 369-377.

17. Ill, C. R., Engvall, E. and Ruoslahti, E. (1984) Adhesion of platelets to laminin in the absence of activation. J. Cell Biol. 99, 2140-2145.

18. Imhof, B. A., Vollmers, H. P., Goodman, S. L., and Birchmeier, W. (1983) Cell-cell interaction and polarity of epithelial cells: specific perturbation using a monoclonal antibody. Cell 35, 667-675.

19. Kleinman, H. K., Klebe, R. J. and Martin, G. R. (1981) Role of collagenous matrices in the adhesion and growth of cells. J. Cell Biol. 88, 473-485.

20. Oesch, B. and Birchmeier, W. (1982) New surface component of fibroblast's focal contacts identified by a monoclonal antibody. Cell 31, 671-679.

21. Pierschbacher, M. D., Hayman, E. G. and Ruoslahti, E. (1981) Location of the cell-attachment site in fibronectin with monoclonal antibodies and proteolytic fragments of the molecule. Cell 26, 259-267.

22. Pierschbacher, M. D., Hayman, E. G. and Ruoslahti, E. (1983) Synthetic peptides with cell attachment activity of fibronectin. Proc. Natl. Acad. Sci. U.S.A. 80, 1224-1227.

23 Pierschbacher, M. D. and Ruoslahti, E. (1984a) Cell attachment activity of fibronectin can be duplicated by small synthetic fragments of the molecule. Nature 309, 30-33.

24. Pierschbacher, M. D. and Ruoslahti, E. (1984b) Variants of the cell recognition site of fibronectin that retain attachment-promoting activity. Proc. Natl. Acad. Sci. U.S.A. 81, 5985-5988.

25. Pytela, R., Pierschbacher, M. D. and Ruoslahti, E. (1985) Identification and isolation of a 140 kilodalton cell surface glycoprotein with properties expected of a fibronectin receptor. Cell. 40, 191-196.

26. Rubin, K., Hook, M. Obrink, B. and Timpl, R. (1981) Substrate adhesion of rat hepatocytes: Mechanism of attachment to collagen substrates. Cell 24, 463–470.

27. Ruoslahti, E., Engvall, E. and Hayman, E. G. (1981) Fibronectin: Current concepts of its structure and function. Col. Rel. Hes. 1, 95–128.

28. Ruoslahti, E., Hayman, E. G., Pierschbacher, M. D. and Engvall, E. (1982) Fibronectin: Purification, immunochemical properties, and biological activities. Meth. Enzymol. 82. 803–831.

29. Terranova, V. P., Rohrbach, D. H. and Martin, G. R. (1980) Role of laminin in the attachment of PAM 212 (epithelial) cells to basement membrane collagen. Cell 22, 719–726.

30. Vaheri, A., Kurkinen, M., Lehto, V. P., Linder, E. and Timpl, R. (1978) Codistribution of pericellular matrix proteins in cultured fibroblasts and loss in transformation: Fibronectin and procollagen. Proc. Natl. Acad. Sci. U.S.A. 75, 4944–4948.

SUMMARY OF THE INVENTION

The present invention is founded upon the discovery that compositions, typically solutions, in which the active ingredient, insofar as the present invention is concerned, consists essentially of the polypeptide characterized by the sequence ARG-GLY-ASP possesses unique and unexpected cell detachment characteristics. The observation critical to this invention is that all cell types among a variety of cell types tested depend for substrate attachment on a mechanism which is sensitive to the inhibition by the ARG-GLY-ASP peptides. It is shown that this is the case in spite of the fact that the ARG-GLY-ASP peptides do not inhibit the attachment promoting activity of all substrate adhesion properties present in the cultures. This makes it possible to use the ARG-GLY-ASP peptides to prevent and reverse the attachment of cells to natural substrates. Typically, the polypeptide is synthetic, as this is the most efficient presently known method of producing the polypeptide in a sufficiently pure state to be highly effective and without competing, interfering or unduly diluting components, i.e. a polypeptide which consists essentially of the active sequence. These polypeptides typically are at least four to six amino acids in length and usually longer, i.e. up to five to ten and even up to thirty amino acids on one or both ends of the ARG-GLY-ASP sequence. Typical of the compositions which consist essentially of the polypeptides suitable for use in this invention are:

X-ARG-GLY-ASP-Y wherein X and Y are amino acid sequences which do not destroy or interfere with the cell detachment activity of the ARG-GLY-ASP sequence, X being typically zero, i.e. no amino acid, or GLY or an amino acid sequence in which GLY is adjacent the ARG of the sequence stated and Y is typically either SER or ALA or an amino acid sequence in which SER or ALA are adjacent the ASP of the stated sequence, X and Y being preferably up to five amino acids and generally no more than about thirty to forty amino acids in length;

ARG-GLY-ASP-SER;

GLY-ARG-GLY-ASP-SER-PRO;

GLY-ARG-GLY-ASP-SER-PRO-CYS
or

GLY-ARG-GLY-ASP-ALA-PRO

The invention may, then, be characterized as a method of controlling the attachment or of effecting the detachment of cells to grown on substrates comprising the steps of contacting a substrate normally capable of accepting cells with cells normally capable of attaching to such substrate and contacting the substrate with a solution containing a polypeptide consisting essentially of the sequence ARG-GLY-ASP. Since different types of cells show different degrees of susceptibility toward the ARG-GLY-ASP peptides, it will also be possible to selectively remove some cells but not others from a given substrate or to prevent the attachment of some cells while permitting others to attach to a substrate.

The invention may also be characterized as a method of producing cells comprising growing cells on a substrate, contacting the cells with a solution containing a polypeptide consisting essentially of the sequence ARG-GLY-ASP, and harvesting cells detached from the substrate.

As expressed above, the term "consisting essentially" as used here means that the polypeptide includes the sequence ARG-GLY-ASP and other amino acids, and possesses the cell detachment activity described hereinafter.

The invention contemplates applications in cell production, fermentation, cell line preparation, cell matrix production, diagnostics, therapy and in a large number of related or encompassed fields. Culture surfaces that promote cell growth and differentiation could be obtained by letting cells deposit matrix material on a surface followed by removal of the cells with the described peptide. The extracellular matrix left behind would be a better material growth surface than the ones now produced by removal of cells with a detergent

DETAILED DESCRIPTION OF THE INVENTION

Figure 1:
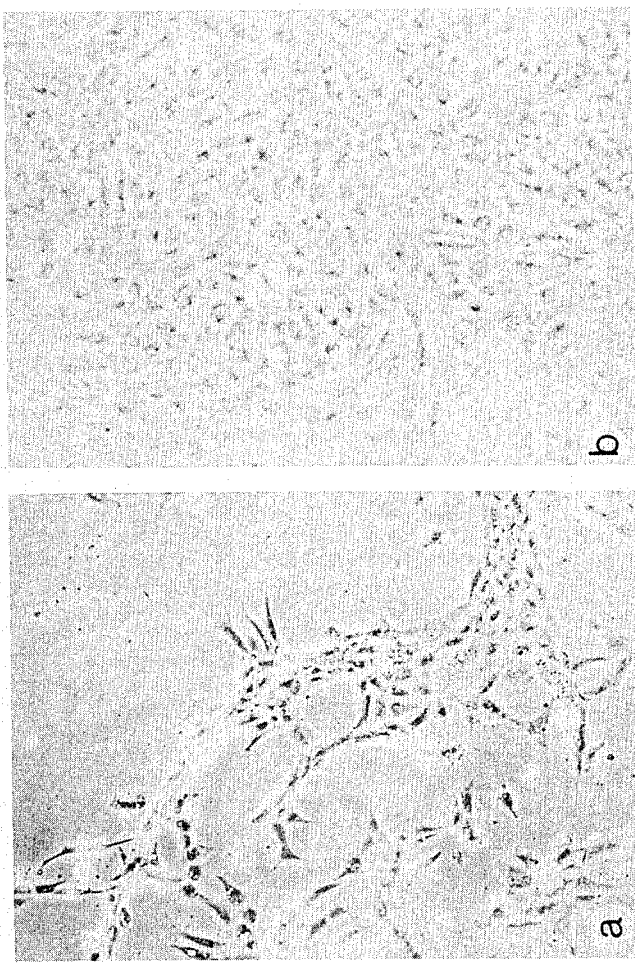
FIGS. 1a and 1b are slide reproductions showing the effect of synthetic peptides on cell cultures. Routine cultures of normal rat kidney cells (NRK) were treated with 1 mg/ml of the synthetic peptide GLY-ARG-GLY-ASP-SER-PRO (GRGDSP) (panel a) or its glutamic acid analog GLY-ARG- GLY-GLU-SER-PRO (GRGESP) (panel b) by adding the peptides to the culture medium. Magnification: ×120. The GRGDSP peptide causes detachment while the GRGESP peptide does- not.

Soluble, synthetic peptides containing the cell recognition sequence Arg-Gly-Asp from fibronectin have previously been shown to interfere with the attachment of normal rat kidney (NRK) cells to fibronectin-coated substrates at millimolar concentrations (Pierschbacher and Ruoslahti, 1984a; 1984b). When the hexapeptide Gly-Arg-Gly-Asp-Ser-Pro (GRGDSP) was added to routine cultures of NRK cells at a concentration of 1 mg/ml (1.5 mM), the cells became detached from the substrate (FIG 1a). The effect was specific, as a control peptide which contains an Asp to Glu substitution and lacks cell attachment activity (Pierschbacher and Ruoslahti, 1984b) had no noticeable effect on the cells at the same concentration (FIG 1b).

Experiments carried out under various conditions showed that the detaching effect of the active peptide was most readily demonstrable when cells were plated 24 hours prior to the addition of the peptide at a density which gave a 70–90% confluent culture at the time the peptide was added. The peptide was also effective in detaching older and denser cultures but the effects were somewhat less pronounced. However, detachment efficiency was increased in all cases if serum was removed before the peptide was added.

Figure 2:
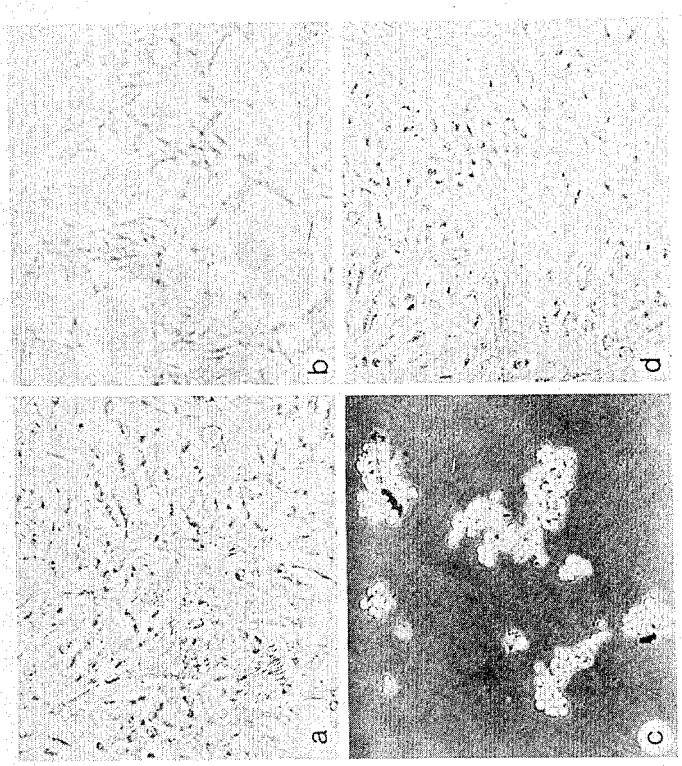
FIGS. 2(a) through (d) are slide reproductions illustrating the time course of cell detachment by Arg-Gly-Asp-containing peptides. NRK cells were cultured for 24 hours on tissue culture dishes in the presence of serum, the culture medium was removed and replaced with serum-free medium containing I mg/ml GRGDSP peptide. The cells were photographed 30 minutes (a), 1.5 hours (b), and 3 hours (c) after the addition of the peptide. No detachment was obtained with a control peptide THR- GLY-ARG-GLY (TGRG, 1 mg/ml) even at I6 hours (d).

When the GRGDSP peptide was added to cultures of NRK cells under the conditions established as more favorable for the detachment (24 hour culture with the peptides added in serum-free medium), the cells began to round up within 30 minutes (FIG. 2a). Holes subsequently appeared in the monolayer as the cells retracted into ridges (FIG. 2b). After a few hours, the cells completely detached from the culture plates forming floating aggregates (FIG. 2c). Cells cultured in the presence of a control peptide (as shown for the tetrapeptide Thr-Gly-Arg-Gly in FIG. 2d) were unaffected even after prolonged exposure to the peptide.

Figure 3:
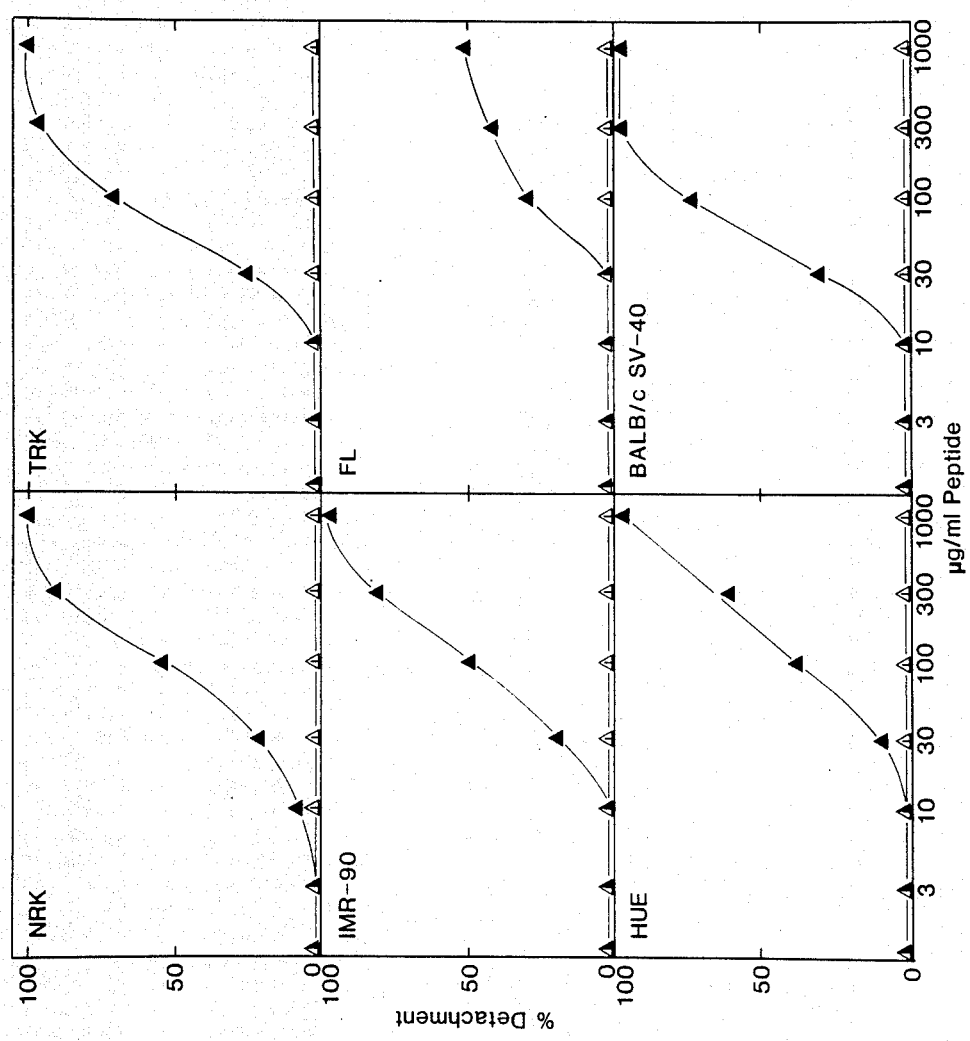
FIGS. 3(a) through 3(d) are graphs depicting the detachment effect of GRGDSP peptide on various cell lines. Subconfluent 24 hour cultures of various cell lines were washed and incubated with serum-free medium containing various concentrations of the GRGDSP peptide (▲) one of the peptides devoid of cell attachment activity listed in Table 1(Δ). After 3 hour incubation at 37°, the cells were washed, fixed with paraformaldehyde, stained and counted. Shown here are normal rat kidney cells, NRK; transformed rat kidney cells, TRK; human fibroblastic cells, IMR-90; epithelial-like human amnion cells, FL; primary human umbilical endothelial cells, HUE; and Simian virus 40-transformed BALB/c 3T3, BALB/c SV40.

Titration of peptides in NRK cell cultures followed by counting of the remaining attached cells showed that the GRGDSP peptide was effective in detaching these cells at and above 10μg/ml (FIG. 3, upper left panel). The activities of the crude and high performance liquid chromatrography (HPLC)-purified GRGDSP peptide were similar. The detachment of the cells was not due to toxicity of the peptide since no cell death could be detected by trypan blue exclusion. Furthermore, when the aggregates were washed free of the peptide and replated, they attached to the dish, and the cells which grew out from these clumps displayed the usual NRK morphology. To study the correlation of detaching capacity with the cell attachment-promoting and attachment-inhibiting effects established previously (Pierschbacher and Ruoslahti, 1984a; 1984b), each of the following listed peptides was tested for its ability to detach cells:

TABLE I

Peptides with cell atachment activity. Pierschbacher and Ruoslahti, 1984a and 1984b.

Arg - Gly - Asp - Ser

Gly - Arg - Gly - Asp - Ser - Pro

Gly - Arg - Gly - Asp - Ser - Pro - Cys

Gly - Arg - Gly - Asp - Ala - Pro

TABLE II

Peptides lacking cell attachment activity. Pierschbacher and Ruoslahti, 1984a and 1984b.

Thr - Gly - Arg - Gly

Arg - Gly - Asn - Ser

Arg - Val - Asp - Ser - Pro - Ala - Cys

Asp - Arg - Glu - Asp - Ser - Arg - Cys

Arg - Val - Asp - Ser - Thr - Ala - Cys

Each of the four Arg-Gly-Asp-containing peptides, which have attachment-promoting activity, detached the cultured NRK cells. In contrast, the five peptides which lack this sequence and do not mediate cell attachment were incapable of detaching the NRK cells.

To determine whether the fibronectin peptides would cause detachment of cells other than the NRK cells, a number of cell types were incubated in the presence of the peptides. The Arg-Gly-Asp-containing peptides were effective in detaching all of the 13 cell strains tested. Examples of the peptide-mediated detachment on these other cell lines are shown in the remaining panels of FIG. 3, and a complete list of the cells tested is given in Example 1. Represented among these lines are normal and transformed cells, established cell lines, as well as primary cultures, fibroblastic, endothelial, and epithelial cell types.

Figure 4:
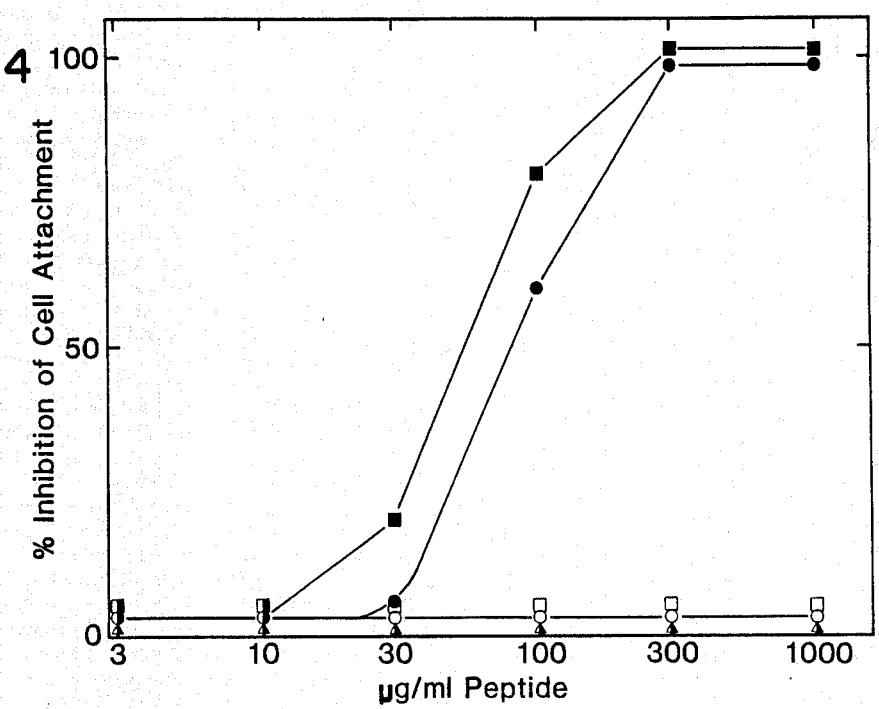
FIG. 4 is a graph depicting the inhibition of cell attachment to defined substrata by synthetic peptides. A single cell suspension of NRK cells was added to dishes coated with 5 μg/ml of fibronectin (●, ○), vitronectin (■, □), or collagen type 1 (▲, △) and the cells were allowed to attach in the presence of various concentrations of the GRGDSP peptide (solid symbols) or an Arg-Gly-Asn-Ser control peptide (open symbols) for 1 hour. Non-attached cells were washed away and the attached cells were fixed, stained and counted.
Figure 5:
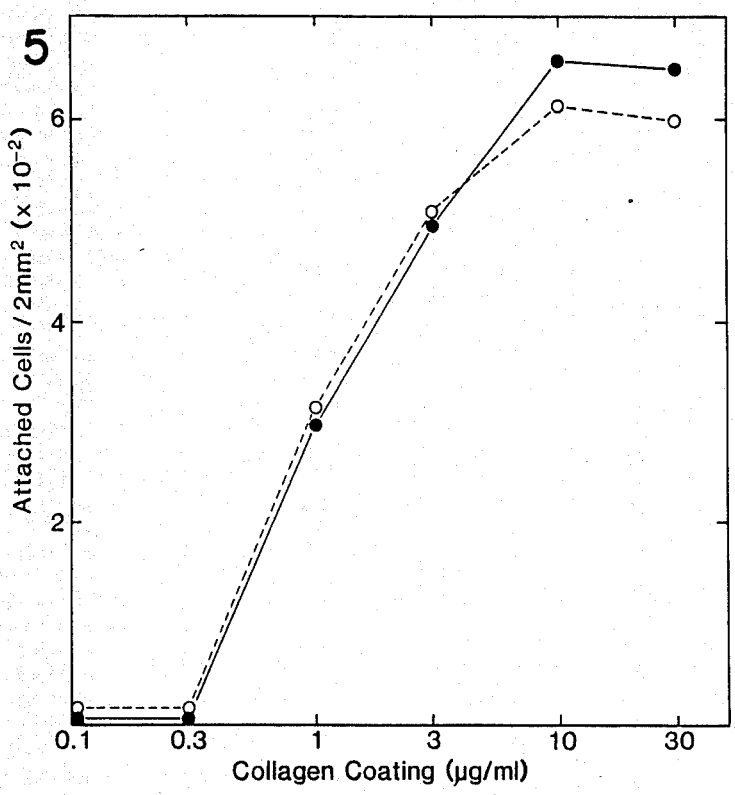
FIG. 5 is a graph depicting attachment of cells to collagen in the presence or absence of GRGDSP peptide. Microtiter wells were coated with different amounts of type I collagen and NRK cells were plated into the wells in the presence of mg/ml of GRGDSP peptide (●) or buffer only (○) Cell attachment was measured as described in the legend of FIG. 4.
Figure 6:
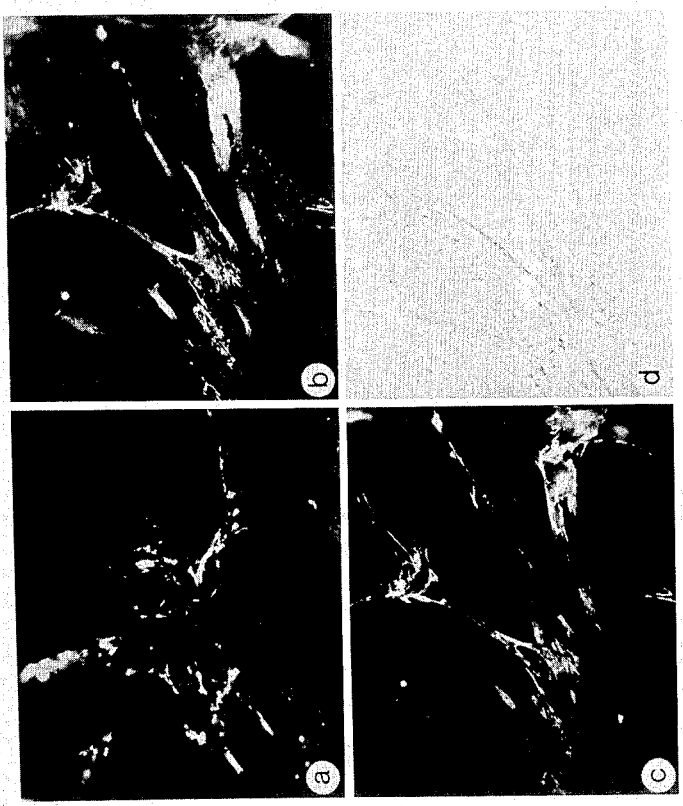
FIGS. 6(a) through 6(d) are slide reproductions depicting the presence of fibronectin and collagen in IMR-90 extracellular matrix. Immunofluorescent staining of a subconfluent 24 hour IMR-90 cell culture for collagen type I (panel a) and a double staining of a similar culture for type VI collagen (b) and fibronectin (c). The type VI collagen fluorescence was detected with fluorescein-conjugated anti-rabbit immunoglobulin G (IgG) and fibronectin with rhodamine-conjugated anti-mouse IgG. (d), phase contrast photograph of the same cells as in panels b and c. Magnification: ×320.

An assay for inhibition of cell attachment similar to the one previously used to show that Arg-Gly-Asp-containing peptides can inhibit attachment of cells to fibronectin (Pierschbacher and Ruoslahti, 1984a) was used to study attachment to vitronectin and collagen. It was found that the GRGDSP and other Arg-Gly-Asp-containing peptides prevented attachment of the NRK test cells to microtiter wells coated with vitronectin at concentrations similar to those that inhibited attachment to fibronectin (FIG. 4). In contrast, the peptides were incapable of preventing the attachment of the cells to wells coated with type I collagen. Titration of the collagen used to coat the dishes showed that the GRGDSP peptide had no effect on the attachment of the NRK cells to such dishes, even at the lowest collagen concentrations (FIG. 5). Similar results were obtained with the human IMR-90 and MRC-5 embryonal fibroblasts.

Cells newly seeded on collagen-coated dishes were refractile to the detaching effect of the Arg-Gly-Asp peptides. To determine whether such cells would remain resistant to the peptides, detachment of cells after different periods of culture on collagen was studied. Such cells became susceptible to the peptides after 24 hours in culture. This acquired susceptibility to the peptides could be due to the cells switching from attachment to collagen to attachment to fibronectin synthesized by the cells themselves. However, since the cells were cultured in the presence of serum, they also might be utilizing fibronectin or vitronectin acquired from the serum and would, because of this, be sensitive to detachment by the Arg-Gly-Asp peptides. Serum vitronectin in particular could be involved because our recent observations show that most of the cell attachment-promoting activity in fetal bovine serum is associated with vitronectin (Hayman, E. G., Pierschbacher, M. D., Suzuki, S., and Ruoslahti, E., submitted for publication).

Figure 7:
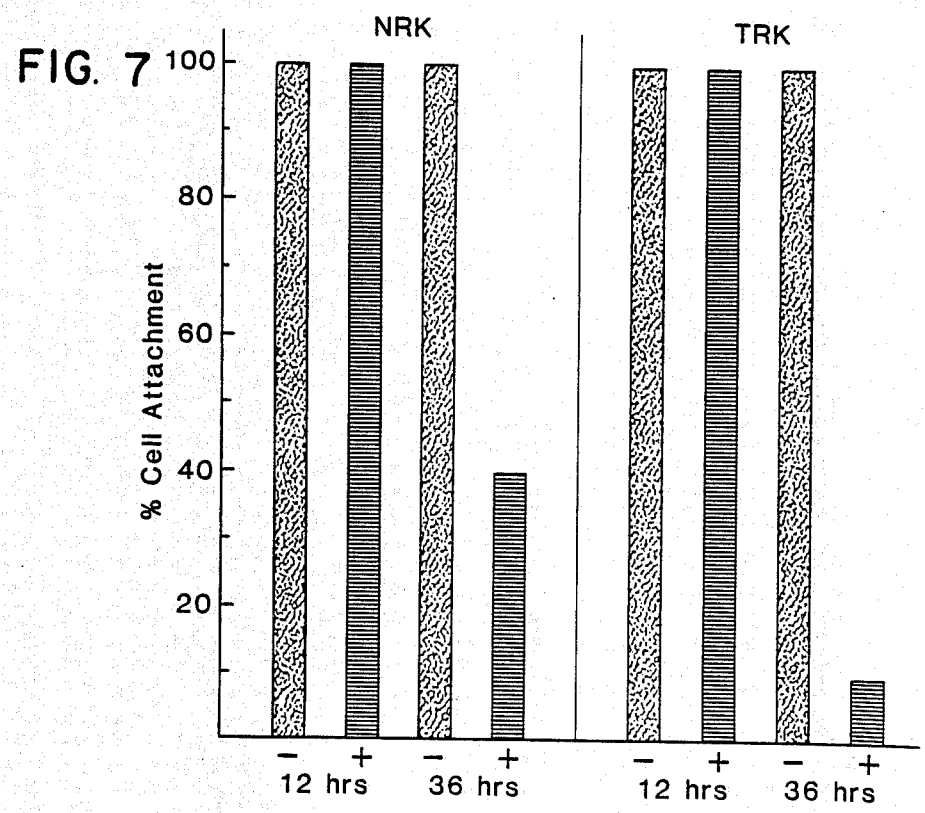
FIG. 7 is a graph depicting the development of susceptibility to peptide detachment in cells cultured on collagens. NRK and TRK cells were cultured in serum-free medium for 12 or 36 hours in 96-well plates coated with collagen type I (10μg/ml). The culture medium was then removed and replaced with fresh serum-free medium with (+) or without (−) 1 mg/ml GRGDSP peptide. After incubation for 3 hours at 37° the cells were counted as in FIG. 3. The assays were run in triplicate which differed less than 10.

The detachment of NRK cells and transformed rat kidney (TRK) cells seeded and cultured on type I collagen in serum-free medium was also studied. Such cells also became susceptible to the detaching effect of the GRGSP peptide after 24 to 36 hours in culture (FIG. 7). Serum, therefore, is not required for these cells to replace their interaction with the collagen with an Arg-Gly-Asp-dependent attachment mechanism.

Figure 8:
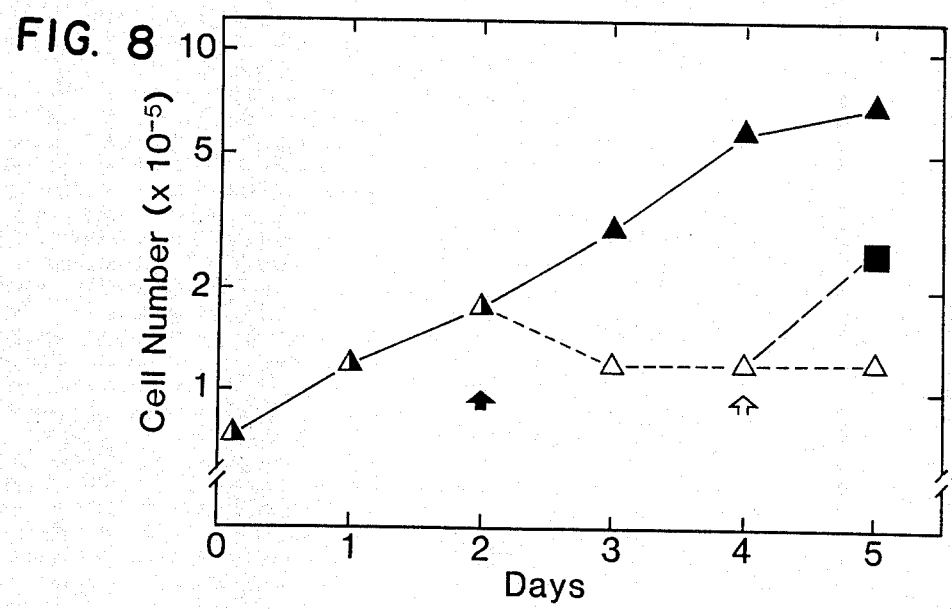
FIG. 8 is a graph depicting the effect of the GRGDSP peptide on growth of NRK cells. Normal rat kidney cells were plated into 60 mm dishes ($0.7 \times 10^5$ cells/dish). On day two (solid arrow), medium was replaced with media containing the GRGDSP peptide (△) or a control peptide )(Asp-Arg-Glu-Asp-Ser-Arg-Cys, ▲), at 1 mg/ml. On day day four (open arrow), media were removed from some cultures in the former group and replaced with normal medium (■). The cell numbers were determined in triplicate cultures.

When NRK cells were cultured in the presence of 1% serum and concentrations of the GRGDSP peptide that detached the cells, the number of live cells remained stationary (FIG. 8). In contrast, in the presence of a control peptide or medium alone, cell number increased with a doubling time of 36 hours.

EXAMPLE I

The following cell lines were cultured in Dulbecco's Modified Eagle's Medium (DME), supplemented with 5% heat-inactivated fetal bovine serum (FBS; Tissue Culture Biologicals, Tulare, CA), glutamine (2mM), penicillin (100 U/ml) and streptomycin (100 μg/ml) (Irvine Scientific, Irvine CA): normal rat kidney (NRK); transformed rat kidney (TRK); mouse, BALB/c 3T3, NIH 3T3, SV40-transformed BALB/c 3T3; human embryonal fibroblastic (MRC-5, IMR-90, WI38); human amniotic (FL), osteosarcoma (MG-63), and fibrosarcoma (HT1080); bovine corneal and aortic endothelial cells. Human umbilical cord endothelial (HUE) cells were isolated using the method of Gimbrone, et al. (1974). They were cultured on fibronectin-coated dishes in DME, 20 % FBS, glutamine, penicillin, streptomycin, fibroblast growth factor (5 μg/ml; Collaborative Research, Lexington, Mass.), and heparin (1 mg/ml; Sigma, St. Louis, Mo.). In some experiments, a defined serum-free medium consisting of DME supplemented with glutamine, penicillin, streptomycin, and 2 mg/ml BSA was used to culture the cells.

Fibronectin (Ruoslahti, et al., 1982) and vitronectin (Hayman, et al., 1983) were isolated from human plasma as previously described. Type I collagen came from Sigma or from Flow Laboratories (Vitrogen 100; Inglewood, Calif.).

Peptides used were synthesized to our specifications at Peninsula Laboratories (San Carlos, Calif.). They were dissolved (10 mg/ml) in DME containing 0.5% bicarbonate buffer, pH 7.0, and diluted immediately for use. The peptide samples were generally used as they were received, containing 80–90% peptide, but when indicated they were first purified by HPLC.

Plastic cell culture dishes (Lindbro, Flow Laboratories) or 96-well microtiter plates (Lindbro) were coated with proteins by incubating the protein dissolved in phosphate buffered saline, pH 7.5, in the dishes or wells for 4 hours at room temperature (Ruoslahti, et al., 1982).

Assays for inhibition of cell attachment were carried out as previously described (Pierschbacher and Ruoslahti, 1984a). The detaching effect of the soluble peptides on cultured cells was studied using cells that had been in culture for 16–48 hours since the previous subculturing. The peptides were added to the culture medium or the culture medium was removed and the cells were washed three times with DMEM containing 2 mg/ml bovine serum albumin (BSA) followed by the addition of the peptides dissolved in DMEM with 2 mg/ml BSA. The effects of the peptides were determined by observing cell morphology and by recording the cell number at indicated times using an Artek cell counter. In control wells only DMEM with 2 mg/ml BSA or standard culture medium was added. The average number of cells in control wells was set at 100%. The assays were run in triplicate.

For cell growth studies, cells were plated in their normal medium, then switched to medium containing 1% FBS with or without peptide.

Cells plated on glass coverslips were processed for immunofluorescence as described previously (Hayman, et al., 1981; Ruoslahti, et al., 1982). The antibodies used for staining were monoclonal 3E3 anti-human fibronectin (Pierschbacher, et al., 1981), rabbit anti-type I collagen (Furthmayr, 1981) and anti-type VI collagen (Hessle and Engvall, 1984).

Discussion

The significance of the present invention is far reaching and of considerable importance in research, diagnostics, and in cell biology generally.

Consider, for example, the value of the method of this invention in the production of cell lines and products of cell lines. The ability to grow cells on substrata and then to remove the cells gently and nontoxically from the substrate opens new avenues of cell production. Some cell lines will propagate only when attached to substrates and others propagate much more efficiently when attached to substrates. Attachment to semipermeable membranes, for example, followed by detachment in accordance with this invention will permit selected nutrients to be provided through the membrane. The production of cell lines for producing a multitude of products, may be greatly simplified by use of the present invention. In some instances, it is advantageous to keep cells detached. An example is the propagation of hybridoma cells producing monoclonal antibodies in a fermentation. The present invention, accordingly, has many and varied values and applications.

The diversity of cell types and culture conditions in which the polypeptides consisting essentially of ARG-GLY-ASP detach cells demonstrate a mechanism which is intrinsic to cells, and is not dependent upon toxicity or secondary mechanism. In vivo treatments using the present invention is, therefore, quite feasible, according to known principles. For example, Boucaut, et al. (1984) have shown that the ARG-GLY-ASP characterized peptide prevented gastrulation in amphibian embryos. In vivo applications of the present invention are considered to include mobilization of bone marrow cells (see Patel, et al., Proc. Nat'l Acad. Sci. U.S.A. (1984) 82, 440-444), prevention and reversal of attachment of dissiminated tumor cells locally, such as in the case of an operation performed in the peritoneal cavity, and prevent of adhesions and scar formations locally, as, for example, in the case of eye operations. Since E.Coli have a surface protein which includes an ARG-GLY-ASP sequence (Pierschbacher & Ruoslahti, 1984c) it may be possible to accomplish prophylactic inhibition of E.coli binding to epithelial cells of the urinary tract or intestine may be accomplished through the principles of this invention, thus preventing or reducing the risk of infection. Diagnosis of E.coli related infections and the treatment of existing infections by the detachment of E.coli may be accomplished within the scope of the present invention. Identification of various pathogenic bacteria strains is also within the scope of the inventive principle of the present invention.

Cell attachment may be controlled as to time, rate, location or amount. For example, it is sometimes desirable to permit cell attachment in some areas before permitting attachment in others. Since the method of this invention is non-toxic and totally reversible, cell attachment may be prevented by bathing a given area with the active polypeptide of this invention during a given period of time and thereafter washing the area free of the polypeptide. Cyclic processes in which cells are permitted to attach, and then are detached and then permitted to attach, in a cyclic stepwise or continuous manner become quite feasible. For example, a continuous belt or ribbon may be carried through a cell production vat, through a cell detachment vat where the cells are harvested, through washing or other treating stations and then back to the cell production vat. Fermentation processes may be greatly accelerated by providing large surface area substrates from which cells are easily harvested using the present invention. The important applications of the present invention are so broad and diversified as almost to defy cataloging at this time.

It is contemplated, based upon present information and techniques, that the polypeptides of this invention will generally be synthetic and can be produced by the Merrifield method, or modifications thereof. Polypeptides which consist essentially of the ARG-GLY-ASP amino acid sequence, as described above, may also be produced by enzyme cleavage and by isolation techniques and, thus produced, would, if sufficiently pure, be considered to be synthetic for purposes of the present invention though perhaps not in the classic definition of synthetic. Typically, however, the better approach is to fully synthesize the polypeptides from the amino acids.

The effective concentration used in the method of this invention is very broad. For example, a few micrograms per milliliter will control the rate of cell attachment in some environments, whereas from 1 to 100 milligrams per ml. may be necessary to detach cells from some substrates. As a general rule, however, effective concentrations will range from 0.1 micrograms per ml. to 100 mg./ml and preferably from 0.1 mg./ml. to 10 mg./ml. of carrier solution. The carrier solution is noncritical. The only requirements being that it be nontoxic to the cells and tissues and that it not contain seriously competing or interfering species. Typical buffer and nutrient solutions are quite satisfactory, as demonstrated hereinbefore.

Industrial Application

This invention finds application in the production of cell lines for research, in diagnosis and therapy, and in the industrial production of cell biological products.

What is claimed is:

1. A method of controlling the Arg-Gly-Asp mediated attachment of animal cells to substrates comprising the steps of:
   (a) contacting a substrate normally capable of accepting cells with cells normally capable of attaching to such substrate; and
   (b) contacting the substrate with a solution containing a polypeptide consisting essentially of the sequence GLY-ARG-GLY-ASP-ALA-PRO.

2. A method of preventing the Arg-Gly-Aap mediated attachment of animal cells to a substrate comprising contacting the cells with a polypeptide consisting essentially of the sequence GLY-ARG-GLY-ASP-ALA-PRO either before contacting the substrate with cells capable of attaching to the substrate or simultaneously with contacting such cells to such substrate.

3. A method of producing animal cells comprising the steps of:
   (a) growing the cells on a substrate;
   (b) contacting the cells with a solution containing a polypeptide consisting essentially of the sequence GLY-ARG-GLY-ASP- ALA-PRO; and
   (c) harvesting cells detached from the substrate.

4. A method for detaching animal cells from a substrate to which they are bound in an Arg-Gly-Asp mediated manner, comprising contacting said bound cells with a solution containing a non-naturally occurring peptide consisting essentially of the amino acid sequence Arg-Gly-Asp-Y, is any amino acid such that the peptide has cell-detachment activity.

5. The method of claim 4 wherein Y further comprises a Ser, Thr, Cys, or Ala residue adjacent said Asp residue.

6. A method for harvesting animal cells grown on a substrate to which said cells attach in an Arg-Gly-Asp mediated manner comprising the steps of:
   contacting said bound cells with a solution containing a non-naturally occurring peptide consisting essentially of the amino acid sequence Arg-Gly-Asp-Y, wherein Y is any amino acid such that the peptide has cell detachment promoting activity; and
   harvesting cells detached from said substrate.

7. The method of claim 6 wherein Y further comprises a Ser, Thr, Cyc or Ala residue adjacent said Asp residue.

8. A method of detaching animal cells from a substrate to which they are bound in an Arg-Gly-Asp mediated manner, comprising contacting said bound cells with a peptide consisting essentially of the amino acid sequence X-Arg-Gly-Asp-Y wherein X is zero to thirty amino acids and Y is one to thirty amino acids, such that the peptide has cell detachment promoting activity.

9. A method for harvesting animal cells grown on a substrate to which said cells attach in an Arg-Gly-Asp mediated manner, comprising the steps of:
   contracting said bound cells with a solution containing a peptide consisting essentially of the amino acid sequence X-Arg-Gly-Asp-Y wherein X is zero to thirty amino acids and Y is one to thirty amino acids, such that the peptide has cell detachment promoting activity; and
   harvesting cells detached from said substrate.

* * * * *

UNITED STATES PATENT AND TRADEMARK OFFICE
CERTIFICATE OF CORRECTION

PATENT NO. : 4,879,237

DATED : 11/7/89

INVENTOR(S) : Ruoslahti et al.

It is certified that error appears in the above-identified patent and that said Letters Patent is hereby corrected as shown below:

On the title page, under item [19], delete "Rudslahti" and insert therefor --Ruoslahti--.

In column 1, after line 28, insert --al. , 1981). Collagens (Rubin et al., 1981), laminin --.

In column 1, line 31, after 1983 insert -- ) --.

In column 1, line 40, before Aggler, insert -- 1. --.

In column 1, line 60, delete "240" and insert therefor -- 2403 --.

In column 1, line 65, delete "4", and insert therefor --34,--.

In column 1, line 68, delete "464" and insert therefor -- 1464 --.

In column 2, line 9, delete "67" and insert therefor --673 --.

In column 2, line 20, delete "400" and insert therefor -- 4003 --.

In column 3, line 5, after "Rel." insert therefor --Res.--.

In column 4, line 3, after cells and before grown, delete "to".

In column 4, line 63, after ), insert -- or --.

In column 5, line 18, before mg, insert -- 1 --.

In column 5, line 41, after 10, insert -- % --.

In column 5, line 62, delete "I" and insert therefor -- 1 --.

UNITED STATES PATENT AND TRADEMARK OFFICE
CERTIFICATE OF CORRECTION

PATENT NO. : 4,879,237

DATED : 11/7/89

INVENTOR(S) : Ruoslahti et al.

It is certified that error appears in the above-identified patent and that said Letters Patent is hereby corrected as shown below:

In column 6, line 43, delete "atachment" and insert therefor -- attachment --.

In column 7, line 58, delete "GRGSP" and insert therefor -- GRGDSP --.

In column 9, line 39, delete "prevent" and insert therefor -- prevention --.

In column 10, line 48, delete "Aap" and insert therefor -- Asp --.

In column 10, line 67, after Y insert -- wherein Y --.

In column 11, line 14, delete "Cyc" and insert therefor -- Cys --.

Signed and Sealed this

Twenty-fifth Day of June, 1991

Attest:

HARRY F. MANBECK, JR.

*Attesting Officer*    Commissioner of Patents and Trademarks